United States Patent
Boualleg et al.

(10) Patent No.: US 10,258,969 B2
(45) Date of Patent: Apr. 16, 2019

(54) CATALYST WITH A MESOPOROUS AND MACROPOROUS CO-MIXED NICKEL ACTIVE PHASE HAVING A MEDIAN MACROPORE DIAMETER OF MORE THAN 300 NM, AND ITS USE IN HYDROGENATION

(71) Applicant: IFP Energies nouvelles, Rueil-Malmaison (FR)

(72) Inventors: Malika Boualleg, Villeurbanne (FR); Anne-Claire Dubreuil, Lyons (FR); Emily Maille, Lyons (FR); Cecile Thomazeau, Lyons (FR)

(73) Assignee: IFP Energies nouvelles, Rueil-Malmaison (FR)

( * ) Notice: Subject to any disclaimer, the term of this patent is extended or adjusted under 35 U.S.C. 154(b) by 79 days.

(21) Appl. No.: 15/318,611

(22) PCT Filed: Jun. 9, 2015

(86) PCT No.: PCT/EP2015/062817
§ 371 (c)(1),
(2) Date: Dec. 13, 2016

(87) PCT Pub. No.: WO2015/189191
PCT Pub. Date: Dec. 17, 2015

(65) Prior Publication Data
US 2017/0120224 A1    May 4, 2017

(30) Foreign Application Priority Data

Jun. 13, 2014  (FR) ..................... 14 55430

(51) Int. Cl.
| | | |
|---|---|---|
| *B01J 21/04* | (2006.01) | |
| *B01J 23/755* | (2006.01) | |
| *B01J 35/10* | (2006.01) | |
| *B01J 37/00* | (2006.01) | |
| *B01J 37/02* | (2006.01) | |
| *B01J 37/03* | (2006.01) | |
| *B01J 37/04* | (2006.01) | |
| *B01J 37/08* | (2006.01) | |
| *B01J 37/16* | (2006.01) | |
| *C07C 5/03* | (2006.01) | |
| *C07C 5/10* | (2006.01) | |
| *B01J 37/20* | (2006.01) | |
| *B01J 33/00* | (2006.01) | |
| *C07C 5/05* | (2006.01) | |
| *C10G 45/36* | (2006.01) | |
| *C10G 45/48* | (2006.01) | |
| *C10G 45/40* | (2006.01) | |
| *C10G 45/52* | (2006.01) | |
| *B01J 35/00* | (2006.01) | |

(52) U.S. Cl.
CPC ............. *B01J 23/755* (2013.01); *B01J 21/04* (2013.01); *B01J 33/00* (2013.01); *B01J 35/006* (2013.01); *B01J 35/108* (2013.01); *B01J 35/1014* (2013.01); *B01J 35/1019* (2013.01); *B01J 35/1038* (2013.01); *B01J 35/1042* (2013.01); *B01J 35/1057* (2013.01); *B01J 35/1061* (2013.01); *B01J 35/1066* (2013.01); *B01J 35/1071* (2013.01); *B01J 37/009* (2013.01); *B01J 37/0236* (2013.01); *B01J 37/03* (2013.01); *B01J 37/036* (2013.01); *B01J 37/04* (2013.01); *B01J 37/08* (2013.01); *B01J 37/16* (2013.01); *B01J 37/20* (2013.01); *C07C 5/03* (2013.01); *C07C 5/05* (2013.01); *C07C 5/10* (2013.01); *C10G 45/36* (2013.01); *C10G 45/40* (2013.01); *C10G 45/48* (2013.01); *C10G 45/52* (2013.01); *C07C 2521/04* (2013.01); *C07C 2523/755* (2013.01); *C07C 2601/14* (2017.05); *C10G 2300/1096* (2013.01); *C10G 2300/705* (2013.01)

(58) Field of Classification Search
None
See application file for complete search history.

(56) References Cited

U.S. PATENT DOCUMENTS 4,301,037 A * 11/1981 Sanchez ................. B01J 21/04
264/142
4,631,265 A   12/1986 Oudejans et al.
(Continued)

FOREIGN PATENT DOCUMENTS

| EP | 0168091 A1 | 1/1986 |
| EP | 0885844 A1 | 12/1998 |
| WO | 2005/028106 A1 | 3/2005 |

OTHER PUBLICATIONS

International Search Report dated Sep. 9, 2015 issued in corresponding PCT/EP2015/062817, 4 pages.

*Primary Examiner* — Colin W. Slifka
(74) *Attorney, Agent, or Firm* — Millen, White, Zelano and Branigan, P.C.

(57) ABSTRACT

The invention concerns a catalyst comprising a calcined oxide matrix which is mainly alumina and an active phase comprising nickel, said active phase being at least partially co-mixed within said calcined oxide matrix which is mainly alumina, the nickel content being in the range 5% to 65% by weight of said element with respect to the total mass of catalyst, said active phase not comprising metal from group VIB, the nickel particles having a diameter of less than 15 nm, said catalyst having a median mesopore diameter in the range 8 nm to 25 nm, a median macropore diameter of more than 300 nm, a mesopore volume, measured by mercury porosimetry, of 0.30 mL/g or more and a total pore volume, measured by mercury porosimetry, of 0.34 mL/g or more. The invention also concerns the process for the preparation of said catalyst, and its use in a hydrogenation process.

13 Claims, No Drawings

(56) References Cited

U.S. PATENT DOCUMENTS

| | | | |
|---|---|---|---|
| 4,920,089 A * | 4/1990 | Van Beek | B01J 21/04 |
| | | | 208/143 |
| 5,478,791 A | 12/1995 | Baldauf et al. | |
| 6,171,573 B1 | 1/2001 | Sato | |
| 6,589,908 B1 | 7/2003 | Ginestra et al. | |
| 2005/0101480 A1 | 5/2005 | Ackerman et al. | |

* cited by examiner

CATALYST WITH A MESOPOROUS AND MACROPOROUS CO-MIXED NICKEL ACTIVE PHASE HAVING A MEDIAN MACROPORE DIAMETER OF MORE THAN 300 NM, AND ITS USE IN HYDROGENATION

FIELD OF THE INVENTION

The invention relates to a co-mixed catalyst with a nickel active phase having a texture and formulation which are favourable to hydrogenation reactions, in particular to reactions for the selective hydrogenation of polyunsaturated compounds, or for the hydrogenation of aromatics. The invention also relates to the process for the preparation of said catalyst, and to its use in hydrogenation reactions.

The most active conventional catalysts in hydrogenation reactions are based on noble metals such as palladium or platinum. These catalysts are used industrially in refining and in petrochemicals for the purification of certain oil cuts by hydrogenation, in particular in reactions for the selective hydrogenation of polyunsaturated molecules such as diolefins, acetylenes or alkenylaromatics, or in reactions for the hydrogenation of aromatics. Palladium has often been substituted by nickel, a metal which is less active than palladium and which thus has to be used in larger quantities in the catalyst. Thus, nickel-based catalysts generally have a metal content of between 5% and 60% by weight of nickel with respect to the catalyst.

The rate of the hydrogenation reaction is governed by several criteria, such as the diffusion of reagents to the surface of the catalyst (external diffusional limitations), the diffusion of reagents into the pores of the support towards the active sites (internal diffusional limitations) and the intrinsic properties of the active phase, such as the size of the metallic particles and the distribution of the active phase within the support.

Regarding the internal diffusional limitations, it is important that the pore distribution of the macropores and mesopores are adapted to the desired reaction in order to ensure diffusion of reagents into the pores of the support towards the active sites, as well as outward diffusion of the products formed. The importance of a suitable pore distribution, and in particular the presence of macropores in a reaction for the selective hydrogenation of a pyrolysis gasoline in the case of a palladium-based catalyst, has been described, for example, by Z. Zhou, T. Zeng, Z. Cheng, W. Yuan, in the AICHE Journal, 2011, Vol. 57, No. 8, pages 2198-2206.

Regarding the size of the metallic particles, it is generally admitted that the activity of the catalyst increases with reducing size of the particles. In addition, it is important to obtain a particle size distribution centred on the optimum value, as well as a narrow distribution about that value.

The frequently high nickel content in hydrogenation catalysts necessitates particular synthesis pathways.

The most conventional pathway for the preparation of such catalysts is impregnation of the support with an aqueous solution of a nickel precursor, generally followed by drying and calcining. Before they are used in hydrogenation reactions, these catalysts are generally reduced in order to be able to obtain an active phase which is in the metallic form (i.e. with an oxidation state of zero). Catalysts based on nickel on alumina prepared by a single impregnation step can generally achieve nickel contents in the range approximately 12% to 15% by weight of nickel, depending on the pore volume of the alumina used. When it is desired to prepare catalysts with a higher nickel content, several successive impregnation steps are often necessary in order to obtain the desired nickel content, followed by at least one drying step, then optionally by a calcining step between each impregnation. Thus, document WO 2011/080515 describes a catalyst based on nickel on alumina which is active in hydrogenation, in particular for aromatics, said catalyst having a nickel content of more than 35% by weight, and a high dispersion of metallic nickel over the surface of an alumina with a very open porosity and a high specific surface area. The catalyst is prepared in at least four successive impregnation steps. The preparation of nickel catalysts with a high nickel content using the impregnation pathway thus involves a concatenation of numerous steps, which increases the associated manufacturing costs.

Another preparation pathway which is also used to obtain catalysts with a high nickel content is co-precipitation. Co-precipitation generally consists of simultaneously pouring both an aluminium salt (for example aluminium nitrate) and a nickel salt (for example nickel nitrate) into a batch reactor. The two salts precipitate out simultaneously. Next, calcining at high temperature is necessary in order to cause the transition of the alumina gel (for example boehmite) into alumina. Using this preparation pathway, contents of up to 70% by weight of nickel are obtained. Catalysts prepared by co-precipitation have been described, for example, in documents U.S. Pat. No. 4,273,680, U.S. Pat. No. 8,518,851 and US 2010/0116717.

Finally, the co-mixing preparation pathway is also known. Co-mixing generally consists of mixing a nickel salt with an alumina gel such as boehmite, said mixture subsequently being shaped, generally by extrusion, then dried and calcined. Document U.S. Pat. No. 5,478,791 describes a catalyst based on nickel on alumina with a nickel content in the range 10% to 60% by weight and a nickel particle size in the range 15 to 60 nm, prepared by co-mixing a nickel compound with an alumina gel, followed by shaping, drying and reduction.

In this context, one of the aims of the present invention is to propose a co-mixed catalyst with a nickel active phase having hydrogenation performances in terms of activity which are at least as good as the catalysts known in the prior art.

More particularly, the invention concerns a catalyst comprising a calcined oxide matrix which is mainly alumina and an active phase comprising nickel, said active phase being at least partially co-mixed within said calcined oxide matrix which is mainly alumina, the nickel content being in the range 5% to 65% by weight of said element with respect to the total mass of catalyst, said active phase not comprising metal from group VIB, the nickel particles having a diameter of less than 15 nm, said catalyst having a median mesopore diameter in the range 8 nm to 25 nm, a median macropore diameter of more than 300 nm, a mesopore volume, measured by mercury porosimetry, of 0.30 mL/g or more and a total pore volume, measured by mercury porosimetry, of 0.34 mL/g or more.

The Applicant has discovered that co-mixing a calcined oxide matrix which is mainly alumina obtained from a particular alumina gel prepared in accordance with the preparation process described below with an active phase comprising nickel means that a catalyst can be obtained which has a pore distribution as well as a nickel particle size which are particularly suited to hydrogenation reactions, in particular to reactions for the selective hydrogenation of polyunsaturated molecules such as diolefins, acetylenes or alkenylaromatics, or to reactions for the hydrogenation of aromatics.

The pore distribution resulting from the preparation process by co-mixing of a calcined oxide matrix which is mainly alumina obtained from a specific alumina gel, and in particular the presence of macropores, means that a porosity can be provided which is particularly suited to favouring the diffusion of reagents into the porous medium then their reaction with the active phase. In fact, in addition to the reduction in the number of steps and thus in manufacturing costs, the advantage of a co-mixing step compared with impregnation is that any risk of reduction of the pore volume, or even partial blocking of the pores of the support during deposition of the active phase and thus the appearance of internal diffusional limitations, is avoided.

The catalyst in accordance with the invention has the particular feature of being able to contain large quantities of active phase. In fact, the fact of preparing the catalyst in accordance with the invention by co-mixing means that this catalyst can be loaded with a large quantity of active phase in a single pass.

It is important to point out that the catalyst in accordance with the invention is structurally distinguished from a catalyst obtained by simple impregnation of a metal precursor onto the alumina support in which the alumina forms the support and the active phase is introduced into the pores of that support. Without wishing to be bound by a particular theory, it appears that the process for the preparation of the catalyst in accordance with the invention by co-mixing a particular porous aluminium oxide with one or more nickel precursors of the active phase means that a composite can be obtained in which the particles of nickel and alumina are intimately mixed, thereby forming the structure of the catalyst per se with a porosity and an active phase content which are adapted to the desired reactions.

In accordance with a variation, the catalyst has a macropore volume in the range 10% to 40% of the total pore volume. In accordance with a variation, the catalyst does not have micropores.

In accordance with a variation, the nickel content is in the range 10% to 34% by weight of said element with respect to the total mass of catalyst.

In accordance with a variation, the nickel particles have a diameter in the range 1.5 to 12 nm.

In accordance with a variation, the active phase is entirely co-mixed. In accordance with another variation, a portion of the active phase is impregnated onto the calcined oxide matrix which is mainly alumina.

The invention also concerns the process for the preparation of said catalyst. The invention also concerns the use of the catalyst in a hydrogenation process in which the catalyst in accordance with the invention or the catalyst which can be prepared in accordance with the preparation process of the invention is brought into contact, in the presence of hydrogen, with a hydrocarbon feed containing polyunsaturated molecules and/or aromatics in a manner such as to obtain an effluent which is at least partially hydrogenated.

DETAILED DESCRIPTION

The Catalyst in Accordance with the Invention

The catalyst in accordance with the invention is in the form of a composite comprising a calcined oxide matrix which is mainly alumina within which the active phase comprising nickel is distributed. The characteristics of the gel which has led to the production of the alumina which is primarily contained in said oxide matrix, as well as the textural properties obtained with the active phase, endow the catalyst in accordance with the invention with its specific properties.

More particularly, the invention concerns a catalyst comprising a calcined oxide matrix which is mainly alumina and an active phase comprising nickel, said active phase being at least partially co-mixed within said calcined oxide matrix which is mainly alumina, the nickel content being in the range 5% to 65% by weight of said element with respect to the total mass of catalyst, said active phase not comprising metal from group VIB, the nickel particles having a diameter of less than 15 nm, said catalyst having a median mesopore diameter in the range 8 nm to 25 nm, a median macropore diameter of more than 300 nm, a mesopore volume, measured by mercury porosimetry, of 0.30 mL/g or more and a total pore volume, measured by mercury porosimetry, of 0.34 mL/g or more.

The nickel content is in the range 5% to 65% by weight of said element with respect to the total mass of catalyst, preferably in the range 8% to 55% by weight, more preferably in the range 10% to 40% by weight, and particularly preferably in the range 10% to 34% by weight. The Ni content is measured by X ray fluorescence.

When the catalyst in accordance with the invention is to be used in a reaction for the selective hydrogenation of polyunsaturated molecules such as diolefins, acetylenes or alkenylaromatics, the nickel content is advantageously in the range 5% to 25% by weight, preferably in the range 8% to 25% by weight, and more preferably in the range 10% to 23% by weight of said element with respect to the total mass of catalyst.

When the catalyst in accordance with the invention is to be used in an aromatics hydrogenation reaction, the nickel content is advantageously in the range 15% to 65% by weight, preferably in the range 18% to 55% by weight, and more preferably in the range 19% to 34% by weight of said element with respect to the total mass of catalyst.

The size of the particles of nickel in the catalyst in accordance with the invention is below 15 nm, preferably in the range 1.5 to 12 nm, and more preferably in the range 2 to 10 nm. The term "size of the particles of nickel" means the diameter of the crystallites of nickel in the oxide form. The diameter of the crystallites of nickel in the oxide form is determined by X ray diffraction starting from the width of the diffraction peak located at the angle $2\theta=43°$ (i.e. in the [200] crystal plane) using the Scherrer relationship. This method, which is used in X ray diffraction on powders or polycrystalline samples, which links the width at mid-height of the diffraction peaks to the particle size, is described in detail in the reference: Appl. Cryst. (1978), 11, 102-113 "Scherrer after sixty years: A survey and some new results in the determination of crystallite size", J. I. Langford and A. J. C. Wilson.

The active phase of the catalyst may also comprise at least one additional metal selected from metals from group VIII, metals from group IB and/or tin. Preferably, the additional metal from group VIII is selected from platinum, ruthenium and rhodium, as well as palladium. Advantageously, the additional metal from group IB is selected from copper, gold and silver. Said additional metal(s) from group VIII and/or group IB is(are) preferably present in a quantity representing 0.01% to 20% by weight of the mass of the catalyst, preferably 0.05% to 10% by weight of the mass of the catalyst and still more preferably 0.05% to 5% by weight of the mass of said catalyst. The tin is preferably present in a quantity representing 0.02% to 15% by weight of the mass of the catalyst, in a manner such that the molar ratio Sn/Ni is in the range 0.01 to 0.2, preferably in the range 0.025 to 0.055, and still more preferably in the range 0.03 to 0.05.

The active phase of the catalyst does not contain any metal from group VIB. In particular, it does not contain molybdenum or tungsten.

Without wishing to be bound by a particular theory, it appears that the catalyst in accordance with the invention exhibits a good compromise between a high pore volume, a high macropore volume, and a small nickel particle size, which therefore means the hydrogenation performances in terms of activity are at least as good as the catalysts which are known in the art.

The catalyst in accordance with the invention also comprises a calcined oxide matrix which is mainly alumina. Said matrix has a calcined alumina content of 90% by weight or more with respect to the total weight of said matrix, optionally supplemented with silica and/or phosphorus in a total amount of at most 10% by weight in equivalents of $SiO_2$ and/or $P_2O_5$, preferably less than 5% by weight, and highly preferably less than 2% by weight with respect to the total weight of said matrix. The silica and/or phosphorus may be introduced using any technique which is known to the person skilled in the art, during the synthesis of the alumina gel or during co-mixing.

Yet more preferably, the calcined oxide matrix which is mainly alumina is constituted by alumina.

Preferably, the alumina present in said matrix is a transition alumina such as a gamma, delta, theta, chi, rho or eta alumina, used alone or as a mixture. More preferably, the alumina is a gamma, delta or theta transition alumina, used alone or as a mixture.

Said catalyst with a co-mixed active phase in accordance with the invention is generally present in any of the forms known to the person skilled in the art, for example in the form of beads (generally having a diameter in the range 1 to 6 mm), extrudates, tablets, or hollow cylinders. Preferably, it is constituted by extrudates with a diameter which is generally in the range 0.5 to 10 mm, preferably in the range 0.8 to 3.2 mm and highly preferably in the range 1.0 to 2.5 mm. It may advantageously be in the form of cylindrical, multilobed, trilobed or quadrilobed extrudates. Preferably, it is trilobed or quadrilobed in form. The form of the lobes could be adjusted using any of the methods known in the art.

The co-mixed catalyst in accordance with the invention has particular textural properties, in particular a specific pore distribution, where the macropore and mesopore volumes are measured by mercury intrusion and the micropore volume is measured by nitrogen adsorption.

The term "macropores" means pores with an opening of more than 50 nm.

The term "mesopores" means pores with an opening in the range 2 nm to 50 nm, limits included.

The term "micropores" means pores with an opening of less than 2 nm.

The term "total pore volume of a catalyst" means the volume measured by mercury intrusion porosimetry in accordance with the ASTM standard D4284-83 at a maximum pressure of 4000 bar (400 MPa), using a surface tension of 484 dyne/cm and a contact angle of 140°. The wetting angle was taken to be 140° because the recommendations in the publication "Techniques de L'ingénieur, traité analyse and caractérisation" [Engineering Techniques— Analysis and Characterization], pages 1050-1055, Jean Charpin and Bernard Rasneur, were followed.

In order to obtain better accuracy, the value for the total pore volume corresponds to the value for the total pore volume measured by mercury intrusion porosimetry measured on the sample minus the value for the total pore volume measured by mercury intrusion porosimetry measured on the same sample for a pressure corresponding to 30 psi (approximately 0.2 MPa).

The volume of the macropores and mesopores is measured by mercury intrusion porosimetry in accordance with the ASTM standard D4284-83 at a maximum pressure of 4000 bar (400 MPa) using a surface tension of 484 dynes/cm and a contact angle of 140°. The value above which the mercury fills all of the intergranular voids is fixed at 0.2 MPa and it is assumed that beyond this value, the mercury penetrates into the pores of the sample.

The macropore volume of the catalyst is defined as being the cumulative volume of mercury introduced at a pressure in the range 0.2 MPa to 30 MPa, corresponding to the volume contained in pores with an apparent diameter of more than 50 nm.

The mesopore volume of a catalyst is defined as being the cumulative volume of mercury introduced at a pressure in the range 30 MPa to 400 MPa, corresponding to the volume contained in pores with an apparent diameter in the range 2 to 50 nm.

The micropore volume is measured using nitrogen porosimetry. Quantitative analysis of the microporosity is carried out using the "t" method (Lippens-De Boer method, 1965), which corresponds to a transform of the initial adsorption isotherm, as described in the publication "Adsorption by powders and porous solids. Principles, methodology and applications" by F. Rouquérol, J. Rouquérol and K. Sing, Academic Press, 1999.

Furthermore, the median mesopore diameter is defined as being the diameter at which all of the pores, from the set of pores constituting the mesopore volume, with a size less than that diameter constitutes 50% of the total mesopore volume determined by mercury intrusion porosimetry.

Further, the median macropore diameter is defined as being the diameter at which all of the pores, from the set of pores constituting the macropore volume, with a size below that diameter constitutes 50% of the total macropore volume determined by mercury intrusion porosimetry.

The term "specific surface area" of a catalyst means the B.E.T. specific surface area determined by nitrogen adsorption in accordance with the ASTM standard D 3663-78 established from the BRUNAUER-EMMETT-TELLER method described in the periodical "The Journal of American Society", 60, 309, (1938).

In the description below, the groups for the chemical elements are given in accordance with the CAS classification (CRC Handbook of Chemistry and Physics, published by CRC press, editor-in-chief D. R. Lide, $81^{st}$ edition, 2000-2001). As an example, group VIII in the CAS classification corresponds to metals in groups 8, 9 and 10 in the new IUPAC classification.

The catalyst in accordance with the invention has a total pore volume of at least 0.34 mL/g, preferably at least 0.40 mL/g, and more preferably in the range 0.45 to 0.85 mL/g.

The catalyst advantageously has a macropore volume in the range 10% to 40% of the total pore volume, preferably in the range 15% to 38% of the total pore volume, and particularly preferably in the range 20% to 35% of the total pore volume.

The mesopore volume of the catalyst is at least 0.30 mL/g, preferably at least 0.35 mL/g, and particularly preferably in the range 0.35 mL/g to 0.55 mL/g.

The median mesopore diameter is in the range 8 nm to 25 nm, preferably in the range 9 to 22 nm, and particularly preferably in the range 10 to 20 nm.

The catalyst has a median macropore diameter of more than 300 nm, preferably in the range 310 to 1500 nm, more preferably in the range 350 to 1000 nm and yet more preferably in the range 390 to 800 nm.

The catalyst in accordance with the present invention has a B.E.T specific surface area of at least 40 m$^2$/g, preferably at least 50 m$^2$/g, and more preferably in the range 55 to 250 m$^2$/g.

Preferably, the catalyst has a low microporosity; highly preferably, it has a zero microporosity.

Preparation Process

The present invention also concerns a process for the preparation of said catalyst in accordance with the invention.

The catalyst with a co-mixed active phase in accordance with the invention is prepared from a specific alumina gel. The particular pore distribution observed in the catalyst is primarily due to the preparation process starting from the specific alumina gel.

The preparation of said alumina gel comprises the following successive steps: a step for dissolving an acidic aluminium precursor, a step for adjusting the pH of the suspension by means of a basic precursor, and a step for co-precipitation of at least one acidic precursor and at least one basic precursor, one of the two at least containing aluminium, and a filtration step. The gel then undergoes a drying step in order to obtain a powder. The powder then undergoes a heat treatment in order to obtain a calcined porous aluminium oxide. The calcined porous aluminium oxide is then mixed with a solution comprising the salt or salts of the precursor(s) of the active phase in order to obtain a paste. This paste is then shaped, then dried in order to obtain a dried catalyst. Next, the dried catalyst optionally undergoes a heat treatment, then is generally reduced and undergoes a passivation treatment.

More particularly, the process for the preparation of the catalyst in accordance with the invention comprises the following steps:

a) a step for dissolving an acidic aluminium precursor selected from aluminium sulphate, aluminium chloride and aluminium nitrate in water, at a temperature in the range 20° C. to 90° C., at a pH in the range 0.5 to 5, for a period in the range 2 to 60 minutes, b) a step for adjusting the pH by adding at least one basic precursor selected from sodium aluminate, potassium aluminate, ammonia, sodium hydroxide and potassium hydroxide to the suspension obtained in step a), at a temperature in the range 20° C. to 90° C., and to a pH in the range 7 to 10, for a period in the range 5 to 30 minutes, c) a step for co-precipitation of the suspension obtained from step b) by adding to the suspension at least one basic precursor selected from sodium aluminate, potassium aluminate, ammonia, sodium hydroxide and potassium hydroxide and at least one acidic precursor selected from aluminium sulphate, aluminium chloride, aluminium nitrate, sulphuric acid, hydrochloric acid and nitric acid, at least one of the basic or acidic precursors comprising aluminium, the relative flow rate of the acidic and basic precursors being selected in a manner such as to obtain a pH of the reaction medium in the range 7 to 10 and the flow rate of the acidic and basic precursors containing aluminium being adjusted in a manner such as to obtain a final concentration of alumina in the suspension in the range 10 to 38 g/L, d) a step for filtration of the suspension obtained from the co-precipitation step c) in order to obtain an alumina gel, e) a step for drying said alumina gel obtained in step d) in order to obtain a powder, f) a step for heat treatment of the powder obtained from step e) at a temperature in the range 500° C. to 1000° C., in the presence or otherwise of a stream of air containing up to 60% by volume of water, for a period in the range 2 to 10 hours, in order to obtain a calcined porous aluminium oxide, g) a step for mixing the calcined porous aluminium oxide obtained from step f) with a solution comprising at least one nickel precursor in order to obtain a paste, h) a step for shaping the paste obtained, i) a step for drying the shaped paste at a temperature in the range 15° C. to less than 250° C., in order to obtain a dried catalyst, j) optionally, a heat treatment of the dried catalyst at a temperature in the range 250° C. to 1000° C. in the presence or absence of water.

Dissolution Step a)

Step a) is a step for dissolving an acidic aluminium precursor selected from aluminium sulphate, aluminium chloride and aluminium nitrate in water, at a temperature in the range 20° C. to 90° C., at a pH in the range 0.5 to 5, for a period in the range 2 to 60 minutes. Step a) is carried out at a temperature in the range 20° C. to 90° C., preferably in the range 20° C. to 75° C., and more preferably in the range 30° C. to 70° C. The pH of the suspension obtained is in the range 0.5 to 5, preferably in the range 1 to 4, and more preferably in the range 1.5 to 3.5. This step advantageously contributes to a quantity of alumina introduced with respect to the final alumina in the range 0.5% to 4%, preferably in the range 1% to 3%, highly preferably in the range 1.5% to 2.5%. The suspension is stirred for a period in the range 2 to 60 minutes, and preferably in the range 5 to 30 minutes.

Step b), pH Adjustment

Step b) for adjusting the pH consists of adding to the suspension obtained in step a) at least one basic precursor selected from sodium aluminate, potassium aluminate, ammonia, sodium hydroxide and potassium hydroxide.

Preferably, the basic precursor is selected from sodium aluminate and potassium aluminate. Highly preferably, the basic precursor is sodium aluminate.

Step b) is carried out at a temperature in the range 20° C. to 90° C., preferably in the range 20° C. to 80° C., and more preferably in the range 30° C. to 70° C., and to a pH in the range 7 to 10, preferably in the range 8 to 10, more preferably in the range 8.5 to 10 and highly preferably in the range 8.7 to 9.9. The duration of pH adjustment step b) is in the range 5 to 30 minutes, preferably in the range 8 to 25 minutes, and highly preferably in the range 10 to 20 minutes.

Co-Precipitation Step c)

Step c) is a step for co-precipitation of the suspension obtained from step b) by adding to this suspension an aqueous solution of at least one basic precursor selected from sodium aluminate, potassium aluminate, ammonia, sodium hydroxide and potassium hydroxide and at least one acidic precursor selected from aluminium sulphate, aluminium chloride, aluminium nitrate, sulphuric acid, hydrochloric acid and nitric acid, at least one of the basic or acidic precursors comprising aluminium, said precursors being selected so as to be identical or otherwise to the precursors introduced in steps a) and b). The relative flow rate of the acidic and basic precursors is selected in a manner such as to obtain a pH for the reaction medium in the range 7 to 10 and the flow rate of the acidic and basic precursors containing aluminium is adjusted in a manner such as to obtain a final alumina concentration in the suspension in the range 10 to 38 g/L, preferably in the range 13 to 35 g/L and more preferably in the range 15 to 33 g/L.

Preferably, the co-precipitation step is carried out at a temperature in the range 20° C. to 90° C., more preferably in the range 30° C. to 70° C.

The co-precipitation step c) is carried out at a pH in the range 7 to 10, preferably in the range 8 to 10, more preferably in the range 8.5 to 10, and highly preferably in the range 8.7 to 9.9.

Co-precipitation step c) is carried out for a period in the range 1 to 60 minutes, and preferably in the range 5 to 45 minutes.

Preferably, said steps a), b) and c) are carried out in the absence of organic additive. Preferably, steps a), b) and c) are operated with stirring.

Filtration Step d)

The process for the preparation of the alumina in accordance with the invention also comprises a step d) for filtration of the suspension obtained at the end of step c) in a manner such as to obtain an alumina gel.

Said filtration step is carried out using methods known to the person skilled in the art.

Said filtration step is advantageously followed by at least one washing step with an aqueous solution, preferably using water and preferably with one to three washing steps, using a quantity of water equal to the quantity of filtered precipitate.

Step e) Drying the Alumina Gel

In accordance with the invention, the alumina gel obtained from the precipitation step c) followed by a filtration step d) is dried in a drying step e) in order to obtain a powder. Said drying step is generally carried out at a temperature of 120° C. or more or by atomization or by any other drying technique known to the person skilled in the art.

In the case in which said drying step e) is carried out by drying at a temperature of 120° C. or more, said drying step d) may advantageously be carried out in a closed or ventilated oven. Preferably, said drying step is operated at a temperature in the range 120° C. to 300° C., highly preferably at a temperature in the range 150° C. to 250° C.

In the case in which said drying step e) is carried out by atomization, the "cake" obtained from the second precipitation step followed by a filtration step is taken up in suspension. Said suspension is then sprayed into fine droplets in a vertical cylindrical vessel in contact with a current of hot air in order to evaporate the water in accordance with the principle which is well known to the person skilled in the art. The powder obtained is entrained by the stream of heat to a cyclone or a bag filter which will separate the air from the powder.

Preferably, in the case in which said drying step e) is carried out by atomization, the atomization is carried out in accordance with the operating protocol described in the publication Asep Bayu Dani Nandiyanto, Kikuo Okuyama, Advanced Powder Technology, 22, 1-19, 2011.

Step f) Heat Treatment of the Powder Obtained from Step e)

In accordance with the invention, the powder obtained from the drying step e) then undergoes a step f) for heat treatment at a temperature in the range 500° C. to 1000° C. for a period which is advantageously in the range 2 to 10 hours, in the presence or otherwise of a stream of air containing up to 60% by volume of water, in order to obtain a calcined porous aluminium oxide.

Said heat treatment may be carried out in the presence of a stream of air containing up to 60% by volume of water, also known as heat or hydrothermal treatment. The term "heat or hydrothermal treatment" means treatment at temperature, respectively in the absence or presence of water. In this latter case, contact with the water can be carried out at atmospheric pressure (steaming) or under autogenous pressure (autoclaving). Several combined cycles of heat or hydrothermal treatments may be carried out. The temperature of said treatments is in the range 500° C. to 1000° C., preferably in the range 540° C. to 850° C.

Said heat treatment step f) can be used to bring about the transition of boehmite into the final alumina. The alumina has a crystallographic structure of the gamma, delta, theta, chi, rho or eta type transition alumina, alone or as a mixture. More preferably, the alumina is a gamma, delta or theta transition alumina, alone or as a mixture. The existence of various crystallographic structures is linked to the conditions of the heat treatment step f).

Step g) Co-Mixing

In this step, the calcined porous aluminium oxide obtained in step f) is mixed with a solution comprising at least one nickel precursor in order to obtain a paste.

The active phase is supplied via one or more solutions containing at least nickel.

Said solution(s) may be aqueous or constituted by an organic solvent, or indeed a mixture of water and at least one organic solvent (for example ethanol or toluene). Preferably, the solution is aqueous. The pH of this solution could be modified by optionally adding an acid. In accordance with another preferred variation, the aqueous solution may contain ammonia or ammonium ions, $NH_4^+$.

Preferably, said nickel precursor is introduced in aqueous solution, for example in the form of the nitrate, carbonate, acetate, chloride, hydroxide, hydroxycarbonate, oxalate, complexes formed by a polyacid or an acid-alcohol and its salts, complexes formed with acetylacetonates, or any other inorganic derivative which is soluble in aqueous solution, which is brought into contact with said calcined porous aluminium oxide. Preferably, nickel nitrate, nickel chloride, nickel acetate or nickel hydroxycarbonate is used as the nickel precursor. Highly preferably, the nickel precursor is nickel nitrate or nickel hydroxycarbonate.

In accordance with another preferred variation, said nickel precursor is introduced in ammoniacal solution by introducing a nickel salt, for example nickel hydroxide or nickel carbonate, in an ammoniacal solution or in a solution of ammonium carbonate or ammonium bicarbonate.

The quantities of the nickel precursor or precursors introduced into the solution are selected in a manner such that the total nickel content is in the range 5% to 65% by weight, preferably in the range 8% to 55% by weight, more preferably in the range 10% to 40% by weight, and particularly preferably in the range 10% to 34% by weight of said element with respect to the total mass of catalyst. The nickel contents are generally adapted to the envisaged hydrogenation reaction, as described above in the paragraph describing the catalyst.

Any other supplemental element may be introduced into the mixing bowl during the co-mixing step, or into the solution containing the metallic salt or salts of the precursors of the active phase.

When it is desired to introduced silica into the matrix, a solution or an emulsion of a silicic precursor may be introduced.

When it is desired to introduce phosphorus into the matrix, a solution of phosphoric acid may be introduced.

When an additional metal selected from metals from group VIII, metals from group IB and/or tin is to be introduced, a salt selected from the nitrate, sulphate, chloride or any other conventional precursor is advantageously employed as the precursor.

An additive, for example a chelating agent of an organic nature, may advantageously be introduced into the solution if the person skilled in the art judges it necessary.

Co-mixing is advantageously carried out in a mixer, for example a mixer of the "Brabender" type which is well known to the person skilled in the art. The calcined alumina powder obtained in step f) and one or more optional supplemental elements are placed in the bowl of the mixer. Next, the solution comprising at least one nickel precursor, optionally one or more supplemental element(s) and optionally deionized water is added with a syringe or with any other means over a period of a few minutes, typically approximately 2 minutes, at a given mixing rate. After obtaining a paste, mixing may be continued for several minutes, for example approximately 15 minutes, at 50 rpm.

The solution comprising at least one nickel precursor may also be added in several batches during this co-mixing phase.

Step h) Shaping

The paste obtained from the co-mixing step g) is then shaped using any shaping technique which is known to the person skilled in the art, for example extrusion or pelletization methods, the oil drop (drop coagulation) method, or by rotary plate granulation.

Preferably, the paste is shaped by extrusion into the form of extrudates, generally with a diameter in the range 0.5 to 10 mm, preferably 0.8 to 3.2 mm, and highly preferably in the range 1.0 to 2.5 mm. This may advantageously be in the form of cylindrical, trilobed or quadrilobed extrudates. Preferably, it will be trilobed or quadrilobed in shape.

Highly preferably, said co-mixing step g) and said shaping step h) are combined into a single mixing-extrusion step. In this case, the paste obtained at the end of mixing may be introduced into a piston extruder through a die with the desired diameter, typically between 0.5 and 10 mm.

Step i) Drying the Shaped Paste

In accordance with the invention, the shaped paste undergoes a drying step i) at a temperature in the range 15° C. to below 250° C., preferably in the range 80° C. to 200° C., using any technique which is known to the person skilled in the art, for a period which is typically in the range 10 minutes to 24 hours. A dried catalyst is obtained.

Step j) Heat Treatment of Dried Catalyst

The catalyst which has been dried in this manner may then undergo a complementary heat treatment or hydrothermal treatment j) at a temperature in the range 250° C. to 1000° C., and preferably in the range 250° C. to 750° C., for a period which is typically in the range 15 minutes to 10 hours, in the presence or otherwise of water. Several combined cycles of heat treatments or hydrothermal treatments may be carried out. After this or these treatment(s), the catalyst precursor comprises nickel in the oxide form, i.e. in the form of NiO.

In the case in which water is to be added, contact with the steam may be carried out under atmospheric pressure (steaming) or under autogenous pressure (autoclaving). In the case of hydrothermal treatment, the water content is preferably in the range 150 to 900 grams per kilogram of dry air, and more preferably in the range 250 to 650 grams per kilogram of dry air.

In one embodiment, in order to increase the overall content of active phase on the catalyst in accordance with the invention, a portion of the metallic precursor(s) may be introduced into the catalyst obtained from step i) or j) or k), using any method known to the person skilled in the art, the most frequently being that of dry impregnation. One or more supplemental element(s) may also be introduced, such as an additional metal selected from the metals from group VIII, the metals from group IB and/or tin, or an additive such as a chelating agent with an organic nature, using any technique known to the person skilled in the art, for example by impregnation. In these cases, said impregnation is advantageously followed by a drying step and optionally by a heat treatment. Drying may be carried out at a temperature in the range 70° C. to 250° C., preferably in the range 80° C. to 200° C., generally for a period in the range 1 to 24 hours. The heat treatment may be carried out at a temperature in the range 200° C. to 1000° C., preferably in the range 250° C. to 750° C., generally for a period in the range 15 minutes to 10 hours. Several impregnations may be carried out, each impregnation advantageously being followed by a drying step and optionally by a heat treatment.

In another embodiment, the totality of the metallic precursor(s) is introduced during the preparation by co-mixing the calcined oxide matrix which is mainly alumina, and no supplemental impregnation step will then be necessary. The metallic precursor(s) of the active phase are entirely co-mixed within the calcined oxide matrix which is mainly alumina.

Step k) Reduction with a Reducing Gas

Prior to using the catalyst in the catalytic reactor and carrying out a hydrogenation process, at least one reducing treatment step k) is advantageously carried out in the presence of a reducing gas after the steps i) or j) in a manner such as to obtain a catalyst comprising nickel which is at least partially in the metallic form.

This treatment can be used to activate said catalyst and form metallic particles, in particular nickel in an oxidation state of zero. Said reduction treatment may be carried out in situ or ex situ, i.e. after or before charging the catalyst into the hydrogenation reactor. Said reduction treatment step k) may be carried out on the catalyst which may or may not have undergone the passivation step l) described below.

The reducing gas is preferably hydrogen. The hydrogen may be used pure or as a mixture (for example, a hydrogen/nitrogen, hydrogen/argon or hydrogen/methane mixture). In the case in which hydrogen is used as a mixture, any proportions may be envisaged.

Said reducing treatment is carried out at a temperature in the range 120° C. to 500° C., preferably in the range 150° C. to 450° C. When the catalyst does not undergo passivation or undergoes a reduction treatment before passivation, the reduction treatment is carried out at a temperature in the range 350° C. to 500° C., preferably in the range 350° C. to 450° C. When the catalyst has previously undergone passivation, the reduction treatment is generally carried out at a temperature in the range 120° C. to 350° C., preferably in the range 150° C. to 350° C.

The duration of the reduction treatment is generally in the range 2 to 40 hours, preferably in the range 3 to 30 hours. The temperature rise to the desired reduction temperature is generally slow, for example fixed at between 0.1 and 10° C./min, preferably between 0.3 and 7° C./min.

The flow rate of hydrogen, expressed in L/hour/gram of catalyst, is in the range 0.1 and 100 L/hour/gram of catalyst, preferably in the range 0.5 to 10 L/hour/gram of catalyst, and more preferably in the range 0.7 to 5 L/hour/gram of catalyst.

Step l) Passivation

Prior to using it in the catalytic reactor, the catalyst in accordance with the invention may optionally undergo a passivation step (step l) using a sulphur-containing or oxygen-containing compound or $CO_2$, before or after the reduction treatment step k). This passivation step may be carried out ex situ or in situ. The passivation step is carried out using methods which are known to the person skilled in the art.

The step for passivation with sulphur can be used to improve the selectivity of the catalysts and prevent runaway when starting up with fresh catalysts. Passivation generally consists of irreversibly poisoning, with the sulphur-containing compound, the most virulent active sites of the nickel which exist on the fresh catalyst, and thus of attenuating the activity of the catalyst in favour of its selectivity. The passivation step is carried out by implementing methods which are known to the person skilled in the art; by way of example, one of the methods described in the patent documents EP 0 466 567, U.S. Pat. No. 5,153,163, FR 2 676 184, WO 2004/098774, EP 0 707 890 may be used. The sulphur-containing compound is, for example, selected from the following compounds: thiophene, thiophane, alkylmonosulphides such as dimethylsulphide, diethylsulphide, dipropylsulphide and propylmethylsulphide, or indeed an organic disulphide with formula HO—$R_1$—S—S—$R_2$—OH such as dithio-diethanol with formula HO—$C_2H_4$—S—S—$C_2H_4$—OH (often known as TDE). The sulphur content is generally in the range 0.1% to 2% by weight of said element with respect to the mass of catalyst.

The step for passivation with an oxygen-containing compound or with $CO_2$ is generally carried out after a prior reduction treatment at high temperature, generally in the range 350° C. to 500° C., and can be used to preserve the metallic phase of the catalyst in the presence of air. A second reduction treatment at a lower temperature, generally in the range 120° C. to 350° C., is then generally carried out. The oxygen-containing compound is generally air or any other stream containing oxygen.

Selective Hydrogenation Process

The present invention also concerns the use of the catalyst in accordance with the invention in a hydrogenation process, and in particular in a process for the selective hydrogenation of polyunsaturated molecules such as diolefins, acetylenes or alkenylaromatics, also known as styrenes.

Mono-unsaturated organic compounds such as, for example, ethylene and propylene, are the basic material for the manufacture of polymers, plastic materials and other added value chemical products. These compounds are obtained from natural gas, naphtha or gas oil which have been treated using steam cracking or catalytic cracking processes. These processes are operated at high temperature and produce, in addition to the desired mono-unsaturated compounds, polyunsaturated organic compounds such as acetylene, propadiene and methylacetylene (or propyne), 1,2-butadiene and 1,3-butadiene, vinylacetylene and ethylacetylene, and other polyunsaturated compounds with a boiling point corresponding to the C5+ gasoline fraction (gasolines containing hydrocarbon compounds containing 5 or more carbon atoms), in particular diolefinic or styrene or indene compounds. These polyunsaturated compounds are highly reactive and lead to unwanted reactions in the polymerization units. Thus, it is necessary to eliminate them before upgrading these cuts.

Selective hydrogenation is the principal treatment developed to specifically eliminate the unwanted polyunsaturated compounds from these hydrocarbon feeds. It can be used to convert polyunsaturated compounds into the corresponding alkenes or aromatics, preventing their total saturation and thus the formation of the corresponding alkanes or naphthenes. In the case of steam cracked gasolines used as the feed, selective hydrogenation can also be used to selectively hydrogenate the alkenylaromatics into aromatics, avoiding hydrogenation of the aromatic rings.

The hydrocarbon feed treated in the selective hydrogenation process has a final boiling point of 250° C. or less and contains at least 2 carbon atoms per molecule and comprises at least one polyunsaturated compound. The term "polyunsaturated compounds" means compounds comprising at least one acetylene function and/or at least one diene function and/or at least one alkenylaromatic function.

More particularly, the feed is selected from the group constituted by a C2 steam cracked cut, a C3 steam cracked cut, a C4 steam cracked cut, a C5 steam cracked cut, and a steam cracked gasoline also known as pyrolysis gasoline. Steam cracked gasoline or pyrolysis gasoline corresponds to a hydrocarbon cut wherein the boiling point is generally in the range 0° C. to 250° C., preferably in the range 10° C. to 220° C. Particular polyunsaturated hydrocarbons to be hydrogenated present in said steam cracked gasoline are diolefinic compounds (butadiene, isoprene, cyclopentadiene, etc), styrene compounds (styrene, alpha-methylstyrene, etc) and indene compounds (indene, etc). The steam cracked gasoline generally comprises the C5-C12 cut with traces of C3, C4, C13, C14, C15 (for example between 0.1% and 3% by weight for each of these cuts). As an example, a feed formed from pyrolysis gasoline generally has a composition as follows: 5% to 25% by weight of paraffins, 40% to 70% by weight of aromatic compounds, 5% to 20% by weight of monoolefins, 5% to 40% by weight of diolefins, 1% to 10% by weight of alkenylaromatic compounds and 20 to 300 ppm by weight of sulphur, the compounds making up to 100%. Preferably, the polyunsaturated hydrocarbon feed treated in accordance with the selective hydrogenation process in accordance with the invention is a steam cracked gasoline.

The selective hydrogenation process in accordance with the invention is intended to eliminate said polyunsaturated hydrocarbons present in said feed to be hydrogenated without hydrogenating the mono-unsaturated hydrocarbons. As an example, when said feed is a C2 cut, the selective hydrogenation process is intended to selectively hydrogenate acetylene. When said feed is a C3 cut, the selective hydrogenation process is intended to selectively hydrogenate propadiene and methylacetylene. In the case of a C4 cut, butadiene, vinylacetylene (VAC) and butyne are intended to be eliminated, and in the case of a C5 cut, pentadienes are intended to be eliminated. When said feed is a steam cracked gasoline, the selective hydrogenation process is intended to selectively hydrogenate said polyunsaturated hydrocarbons present in said feed to be treated in a manner such that the diolefinic compounds are partially hydrogenated into monoolefins and the styrene and indene compounds are partially hydrogenated into corresponding aromatic compounds, avoiding hydrogenation of the aromatic rings.

The selective hydrogenation process is, for example, carried out using injection technology, in upflow or downflow mode for the feed of polyunsaturated hydrocarbons and hydrogen in at least one fixed bed reactor. Said reactor may be of the isothermal or adiabatic type. An adiabatic reactor is preferred. The feed of polyunsaturated hydrocarbons may advantageously be diluted by means of one or more re-injection(s) of effluent obtained from said reactor in which the selective hydrogenation reaction takes place, at various points of the reactor, located between the inlet and the outlet of the reactor in order to limit the temperature gradient in the reactor. The selective hydrogenation process in accordance with the invention may also advantageously be carried out using the technology of installing at least said supported catalyst in a reactive distillation column or in exchanger-reactors. The stream of hydrogen may be introduced at the same time as the feed to be hydrogenated and/or at one or more different points of the reactor.

The selective hydrogenation of the C2, C3, C4, C5 and C5+ cuts may be carried out in the gas phase or in the liquid phase, preferably in the liquid phase for the C3, C4, C5 and C5+ cuts. In fact, a liquid phase reaction can be used to reduce the energy costs and increase the cycle time of the catalyst.

In general, selective hydrogenation is carried out at a temperature in the range 0° C. to 500° C., at a pressure in the range 0.1 to 20 MPa, at a hydrogen/(polyunsaturated compounds to be hydrogenated) molar ratio in the range 0.1 to 10 and at an hourly space velocity, HSV (defined as the ratio of the volume flow rate of feed to the volume of catalyst) in the range 0.1 to 200 $h^{-1}$ for a liquid feed, in the range 100 to 15000 $h^{-1}$ for a gaseous feed of a hydrocarbon feed containing polyunsaturated compounds containing at least 2 carbon atoms per molecule and having a final boiling point of 250° C. or less.

Preferably, a selective hydrogenation process is carried out in which the feed is a steam cracked gasoline comprising polyunsaturated compounds, the molar ratio of (hydrogen)/(polyunsaturated compounds to be hydrogenated) generally being in the range 1 to 2, the temperature generally being in the range 40° C. to 200° C., preferably in the range 50° C. to 180° C., the hourly space velocity (HSV) generally being in the range 0.5 to 50 $h^{-1}$, preferably in the range 1 to 20 $h^{-1}$, and the pressure generally being in the range 0.3 to 6.5 MPa, preferably in the range 2.0 to 3.5 MPa. The flow rate of hydrogen is adjusted in order to provide a sufficient quantity to theoretically hydrogenate all of the polyunsaturated compounds and to maintain an excess of hydrogen at the reactor outlet.

Aromatics Hydrogenation Process

The present invention also concerns the use of the catalyst in accordance with the invention in a hydrogenation process and in particular in a process for the hydrogenation of aromatics in order to transform the aromatic compounds of the oil or petrochemical cuts by conversion of the aromatic rings into naphthene rings.

The hydrocarbon feed treated in the process for the hydrogenation of aromatics has a final boiling point of 650° C. or less, generally in the range 20° C. to 650° C., preferably in the range 20° C. to 450° C., and contains at least one aromatic or polyaromatic compound. Examples of oil or petrochemicals cuts containing aromatic compounds which may be cited are kerosene, light gas oil, heavy gas oil and cracked distillates such as FCC recycled oil, gas oil from the cokefaction unit, hydrocracked distillates, and the reformate from catalytic reforming.

The aromatic hydrocarbons content in a feed treated in the hydrogenation process is generally in the range 0.1% to 80% by weight, preferably in the range 1% to 50% by weight, and particularly preferably in the range 2% to 35% by weight, the percentage by weight being based on the total weight of the hydrocarbon feed. The aromatics present are, for example, benzene or alkylaromatics such as toluene, ethylbenzene, o-xylene, m-xylene or p-xylene, or indeed aromatics containing several aromatic rings (polyaromatics) such as naphthalene.

The sulphur or chlorine content of the feed is generally less than 5000 ppm by weight of sulphur or chlorine respectively, preferably less than 100 ppm by weight, and more particularly preferably less than 10 ppm.

The aromatics hydrogenation process may be carried out using technology such as that described in the selective hydrogenation section.

Aromatics hydrogenation may be carried out in the gas phase or in the liquid phase, preferably in the liquid phase. In general, hydrogenation of the aromatics is carried out at a temperature in the range 30° C. to 350° C., preferably in the range 50° C. to 325° C., at a pressure in the range 0.1 to 20 MPa, preferably in the range 0.5 to 10 MPa, at a molar ratio of hydrogen/(aromatic compounds to be hydrogenated) of between 0.1 and 10, and at an hourly space velocity, HSV, in the range 0.05 to 50 $h^{-1}$, preferably in the range 0.1 to 10 $h^{-1}$ of a hydrocarbon feed containing aromatic compounds and having a final boiling point of 650° C. or less. The flow rate of hydrogen is adjusted in order to provide a sufficient quantity to theoretically hydrogenate all of the polyunsaturated compounds and to maintain an excess of hydrogen at the reactor outlet.

The conversion of aromatics or polyaromatic compounds is generally more than 20% molar, preferably more than 40% molar, more preferably more than 80% molar, and particularly preferably more than 90% molar of aromatic or polyaromatic compounds contained in the hydrocarbon feed. The conversion is calculated by dividing the difference between the total moles of the aromatic or polyaromatic compounds in the hydrocarbon feed and in the product by the total moles of aromatic or polyaromatic compounds in the hydrocarbon feed.

In accordance with a particular variation, the catalyst in accordance with the invention is used in a process for the hydrogenation of a hydrocarbon feed containing benzene such as, for example, the reformate obtained from a catalytic reforming unit. The benzene content is generally in the range 0.1% to 40% by weight, preferably in the range 0.5% to 35% by weight, and particularly preferably in the range 2% to 30% by weight, the percentage by weight being based on the total weight of the hydrocarbon feed.

The sulphur or chlorine content of the feed is generally less than 10 ppm by weight of sulphur or chlorine respectively, preferably less than 2 ppm by weight.

The feed containing benzene may be hydrogenated in the gas phase or in the liquid phase, preferably in the liquid phase. When it is carried out in the liquid phase, a solvent may be present. In general, the benzene is hydrogenated at a temperature in the range 30° C. to 250° C., preferably in the range 50° C. to 200° C., and more preferably in the range 80° C. to 180° C., at a pressure in the range 0.1 to 10 MPa, preferably in the range 0.5 to 4 MPa, at a molar ratio of hydrogen/(benzene) in the range 0.1 to 10 and at an hourly space velocity, HSV, in the range 0.05 to 50 $h^{-1}$, preferably in the range 0.5 to 10 $h^{-1}$.

The benzene conversion is generally more than 50% molar, preferably more than 80% molar, more preferably more than 90% molar and particularly preferably more than 98% molar.

The invention will now be illustrated in the following examples.

Example 1: Preparation of an Aqueous Solution of Ni Precursors

The aqueous solution of Ni precursors (solution S) used to prepare the catalysts A, B, C and D was prepared by dissolving 46.1 g of nickel nitrate ($NiNO_3$, supplier: Strem Chemicals®) in a volume of 13 mL of distilled water. The solution S was obtained which had a NiO concentration of 20.1% by weight (with respect to the mass of the solution).

Example 2: Preparation of Co-Mixed Catalyst a in Accordance with the Invention Catalyst A in accordance with the invention was prepared by co-mixing an alumina Al and the solution S of Ni precursors.

Alumina Al in accordance with the invention was synthesised in a laboratory reactor with a capacity of approximately 7000 mL. The synthesis was carried out at 70° C. and with stirring, in six steps denoted a) to f) below. 5 L of solution with a concentration fixed at 27 g/L of alumina in the final suspension (obtained at the end of step c) and with a degree of contribution from the first step a) of 2.1% of the total alumina was to be prepared.

a) Dissolution: 70 mL of aluminium sulphate $Al_2(SO_4)_3$ was introduced all at once into the reactor containing a starter of 1679 mL of water. The change in pH, which remained between 2.5 and 3, was monitored for 10 minutes. This step contributed to the introduction of 2.1% of alumina with respect to the total mass of alumina formed at the end of the synthesis of the gel. Stirring of the solution was continued for a period of 10 minutes.

b) Adjustment of pH: approximately 70 mL of sodium aluminate, NaAOO, was added gradually. The aim was to obtain a pH in the range 7 to 10 over a period of 5 to 15 minutes.

c) Co-precipitation: Over 30 minutes, the following were added to the suspension obtained from step b):
   1020 mL of aluminium sulphate $Al_2(SO_4)_3$, i.e. a flow rate of 34 mL/min,
   1020 mL of sodium aluminate NaAlOO, i.e. a flow rate of 34 mL/min,
   1150 mL of distilled water, i.e. a flow rate of 38.3 mL/min. The pH was in the range 8.7 to 9.9.

d) Filtration: the suspension obtained from step c) was filtered by displacement on a Buchner P4 frit type apparatus and washed several times with distilled water. An alumina gel was obtained.

e) Drying: the alumina gel obtained from step d) was oven dried overnight at 200° C.

f) Heat treatment: the powder obtained from step e) was then calcined at 750° C. for 2 hours in order to cause the boehmite to be transformed into alumina. The alumina Al was then obtained.

The catalyst A was then prepared from the alumina Al and the solution S of Ni precursors, prepared as above, during the following four steps, denoted g) to j):

g) Co-mixing: A "Brabender" mixer was used with an 80 $cm^3$ bowl and a mixing speed of 30 rpm. The alumina powder Al was placed in the bowl of the mixer. Next, the solution S of Ni precursors was added using a syringe over approximately 2 minutes at 15 rpm. After obtaining a paste, mixing was maintained for 15 minutes at 50 rpm.

h) Extrusion: The paste obtained was introduced into a piston extruder and extruded through a die with a diameter of 2.1 mm at 50 mm/min.

i) Drying: The extrudates obtained thereby were then oven dried overnight at 80° C. A dried catalyst was obtained.

j) Heat treatment: The dried catalyst was then calcined in a tube furnace in a stream of air of 1 L/h/g of catalyst, at 450° C. for 2 hours (temperature ramp-up 5° C./min). The calcined catalyst A was then obtained.

The characteristics of the calcined catalyst A obtained in this manner are reported in Table 1 below.

TABLE 1

Properties of catalysts A (in accordance with the invention), and B, C and D (comparative)

| | A In accordance with the invention | B Comparative | C Comparative | D Comparative |
|---|---|---|---|---|
| Alumina precursor | Calcined | Not calcined | Calcined | Calcined |
| Mode of introduction of Ni | Co-mixing | Co-mixing | Dry impregnation | Co-mixing |
| Ni (% by weight) | 22.3 | 23.7 | 23.2 | 19.4 |
| B.E.T. specific surface area ($m^2/g$) | 175 | 243 | 156 | 183 |
| Total pore volume (mL/g) | 0.62 | 0.57 | 0.66 | 0.84 |
| Mesopore volume (mL/g) | 0.42 | 0.28 | 0.47 | 0.38 |
| Median mesopore volume (nm) | 10.5 | 7.1 | 11.5 | 7.4 |
| Macropore volume (mL/g and % of total pore volume) | 0.20 / 32% | 0.29 / 51% | 0.19 / 29% | 0.46 / 55% |
| Median macropore volume (nm) | 435 | 1425 | 638 | 1630 |
| Micropore volume (mL/g) | 0 | 0.18 | 0 | 0 |
| Size of crystallites of NiO (nm) | 9.5 | 14.8 | 15.6 | 11.2 |

Example 3: Preparation of Co-Mixed Catalyst B from Boehmite (Comparative)

Catalyst B was prepared by co-mixing boehmite (non-calcined alumina gel) and the solution S of Ni precursors.

The boehmite was synthesized in a laboratory reactor with a capacity of approximately 7000 mL by following the first five steps, steps a) to e), of Example 2 described above. In the same manner as in Example 2 described above, the synthesis was carried out at 70° C. and with stirring, and 5 L of solution with a fixed concentration of 27 g/L of alumina in the final suspension (obtained at the end of step c) and with a degree of contribution from the first step a) of 2.1% of the total alumina was to be obtained. The operating conditions for the five steps a) to e) were strictly identical to those described in Example 2 above. A boehmite powder B1 was obtained from step e). This boehmite powder B1 was then mixed with the solution S of Ni precursors (described in Example 1). No calcining was carried out between step e) and the co-mixing step.

Catalyst B was then prepared by following the four steps g) to j) described in Example 2. The operating conditions were strictly identical, with the exception of the following two points:

In the co-mixing step g), the boehmite powder B1 was mixed with the solution S of Ni precursors.

In the calcining step j), calcining was carried out at 750° C. in order to transform the boehmite into alumina. This high temperature calcining gave rise to refractory nickel aluminate-type phases.

The characteristics of the calcined catalyst B obtained in this manner are reported in Table 1. Compared with catalyst A, the macropore volume was much higher, the mesopore volume and the median mesopore diameter were much lower. Catalyst B also had microporosity, in contrast to catalyst A. Catalyst B also had NiO crystallites which were much bigger in size than those of catalyst A.

Example 4: Preparation of Catalyst C by Dry Impregnation of an Alumina Support (Comparative)

Catalyst C was prepared by dry impregnation of the alumina Al described in Example 2, with the solution S of Ni precursors.

Alumina Al was synthesized by following the six steps, steps a) to f), of Example 2 described above. The operating conditions were strictly identical. However, a step for shaping the dried alumina gel obtained from step e) was inserted between steps e) and f): this powder was shaped with a "Brabender" type mixer with an acid content of 1% (total acid content, expressed with respect to the dry alumina), a degree of neutralization of 20% and acidic and basic losses on ignition of 62% and 64% respectively. Next, extrusion was carried out on a piston extruder through a die with a diameter of 2.1 mm. Following extrusion, the extrudates were dried overnight at 80° C. At the end of the calcining step f), extrudates of alumina Al were obtained.

The alumina Al was then impregnated with the solution S of Ni precursors, described in Example 1, in accordance with the method known as the dry impregnation method; a volume of 11.5 mL of solution S was added dropwise to a mass of 10.5 g of alumina Al, over a period of 10 minutes. After impregnation, the solid was oven dried at 120° C. overnight, then it was calcined in a stream of air of 1 L/h/g of catalyst, at 450° C. for 2 hours (temperature ramp-up 5° C./min). The calcined catalyst C was obtained thereby.

The characteristics of the calcined catalyst C obtained in this manner are reported in Table 1. It had NiO crystallites which were much bigger in size that those of catalyst A.

Example 5: Preparation of Co-Mixed Catalyst D Starting from an Alumina (Comparative)

The catalyst D was prepared by co-mixing an alumina D1 and the solution S of Ni precursors.

The alumina D1 was synthesized in a 5 L reactor in six steps, denoted a) to f) below. The concentration of acidic and basic aluminium precursors was as follows: aluminium sulphate $Al_2(SO_4)_3$, 102 g/L in $Al_2O_3$ equivalents and sodium aluminate NaAlOO, 155 g/L in $Al_2O_3$ equivalents. The intention was to obtain a final concentration of alumina of 45 g/L in the suspension obtained at the end of the second precipitation step c).

a) A first precipitation of aluminium sulphate $Al_2(SO_4)_3$ and sodium aluminate NaAlOO over 8 minutes at 30° C., pH=9.1, and with a percentage completion of 20%. This percentage completion corresponds to the proportion of alumina formed during this first step.

b) A rise in temperature from 30° C. to 70° C. over 20 to 30 minutes.

c) A second precipitation of aluminium sulphate $Al_2(SO_4)_3$ and sodium aluminate NaAlOO over 30 minutes at 70° C., pH=9.1, and with a percentage completion of 80%. This percentage completion corresponds to the proportion of alumina formed during this second precipitation step.

d) A filtration of the suspension obtained from step c) by displacement on a Buchner P4 frit type apparatus followed by washing three times in succession with 5 L of distilled water.

e) A step for drying the alumina gel overnight at 120° C.

f) A step for calcining the powder obtained from step e) at 750° C. for 2 hours. The alumina D1 was obtained.

Catalyst D was then prepared by co-mixing the alumina D1 and the solution S of Ni precursors described in Example 1 in accordance with the four steps g) to j) described in Example 2. The operating conditions were strictly identical. The calcined catalyst D was obtained thereby from step j).

The characteristics of the calcined catalyst D obtained in this manner are reported in Table 1. This catalyst had a much higher macropore volume than that of catalyst A, as well as a mesopore volume and a median mesopore diameter which were lower than those of catalyst A. It also had NiO crystallites which were bigger in size than those of catalyst A.

Example 6: Evaluation of Catalytic Properties of Catalysts a, B, C and D in the Selective Hydrogenation of a Mixture Containing Styrene and Isoprene Catalysts A, B, C and D described in the above examples were tested as regards the reaction for the selective hydrogenation of a mixture containing styrene and isoprene.

The composition of the feed to be selectively hydrogenated was as follows: 8% by weight styrene (supplied by Sigma Aldrich®, purity 99%), 8% by weight isoprene (supplied by Sigma Aldrich®, purity 99%), 84% by weight n-heptane (solvent) (supplied by VWR®, purity >99%, Chromanorm, HPLC). This feed also contained very small quantities of sulphur-containing compounds: 10 ppm by weight of sulphur introduced in the form of pentanethiol (supplied by Fluka®, purity >97%) and 100 ppm by weight of sulphur introduced in the form of thiophene (supplied by Merck®, purity 99%). This composition corresponded to the initial composition of the reaction mixture. This mixture of model molecules was representative of a pyrolysis gasoline.

The selective hydrogenation reaction was carried out in a 500 mL autoclave of stainless steel provided with a magnetically driven mechanical stirrer and which could function under a maximum pressure of 100 bar and at temperatures in the range 5° C. to 200° C.

Prior to introducing it into the autoclave, a quantity of 3 mL of catalyst was reduced ex situ in a stream of hydrogen of 1 L/h/g of catalyst, at 400° C. for 16 hours (temperature ramp-up 1° C./min), then it was transferred into the autoclave with the exclusion of air. After adding 214 mL of n-heptane (supplier VWR®, purity >99%, Chromanorm, HPLC), the autoclave was closed, purged then pressurized to 35 bar (3.5 MPa) with hydrogen and heated to the test temperature of 30° C. At time t=0, approximately 30 g of a mixture containing styrene, isoprene, n-heptane, pentanethiol and thiophene was introduced into the autoclave. The reaction mixture then had the composition described above and stirring was commenced at 1600 rpm. The pressure in the autoclave was kept constant at 35 bar (3.5 MPa) with the aid of a reserve bottle located upstream of the reactor.

The progress of the reaction was monitored by analyzing samples from the reaction medium at regular time intervals: the styrene was hydrogenated to ethylbenzene without hydrogenation of the aromatic ring, and the isoprene was hydrogenated to methylbutenes. If the reaction was prolonged longer than necessary, the methylbutenes were in turn hydrogenated into isopentane. The hydrogen consumption was also monitored with time by the reduction of pressure in a reserve bottle located upstream of the reactor. The catalytic activity was expressed in moles of $H_2$ consumed per minute and per gram of Ni.

The catalytic activities measured for catalysts A, B, C and D are reported in Table 2 below. They are with respect to the catalytic activity measured for catalyst A ($A_{HYD1}$).

TABLE 2

Comparison of performances in selective hydrogenation of a mixture containing styrene and isoprene ($A_{HYD1}$) and in the hydrogenation of toluene ($A_{HYD2}$)

| Catalyst | In accordance? | State of aluminium precursor | Mode of introduction of Ni precursors | $A_{HYD1}$ (%) | $A_{HYD2}$ (%) |
|---|---|---|---|---|---|
| A | Yes | Calcined | Co-mixing | 100 | 100 |
| B | No | Dried | Co-mixing | 31.7 | 21.9 |
| C | No | Calcined | Dry impregnation | 66.7 | 67.2 |
| D | No | Calcined | Co-mixing | 80.6 | 77.5 |

This clearly demonstrates the improved performances of catalyst A prepared in accordance with the invention. Preparation by co-mixing alumina means that crystallites of NiO can be obtained which are smaller, and thus the catalytic performances are improved (compared with catalyst C). In contrast, preparation by co-mixing of boehmite (catalyst B) results in a major reduction in the catalytic performances because of the presence of big crystallites of NiO and refractory phases (of the nickel aluminate type) formed during high temperature calcining. Adding the specific porosity properties (in terms of the median diameter of the mesopores, the median diameter of the macropores and the macropore volume) to the alumina gel used to prepare the catalyst A in accordance with the invention is illustrated by comparison with catalyst D.

Example 7: Evaluation of Catalytic Properties of Catalysts A, B, C and D in the Hydrogenation of Toluene Catalysts A, B, C and D described in the above examples were also tested as regards the toluene hydrogenation reaction.

The selective hydrogenation reaction was operated in the same autoclave as that described for Example 6.

Prior to introducing it into the autoclave, a quantity of 2 mL of catalyst was reduced ex situ in a stream of hydrogen of 1 L/h/g of catalyst, at 400° C. for 16 hours (temperature ramp-up 1° C./min), then it was transferred into the autoclave with the exclusion of air. After adding 216 mL of n-heptane (supplier VWR®, purity >99%, Chromanorm, HPLC), the autoclave was closed, purged, then pressurized to 35 bar (3.5 MPa) of hydrogen and heated to the test temperature of 80° C. At time t=0, approximately 26 g of toluene (supplier SDS®, purity >99.8%) was introduced into the autoclave (the initial composition of the reaction mixture was thus: toluene 6% by weight/n-heptane, 94% by weight) and stirring was commenced at 1600 rpm. The pressure was kept constant at 35 bar (3.5 MPa) in the autoclave with the aid of a reserve bottle located upstream of the reactor.

The progress of the reaction was monitored by testing analyzing samples from the reaction medium at regular time intervals: the toluene was completely hydrogenated to methylcyclohexane. The hydrogen consumption was also monitored with time by the reduction of pressure in a reserve bottle located upstream of the reactor. The catalytic activity was expressed in moles of $H_2$ consumed per minute and per gram of Ni.

The catalytic activities measured for catalysts A, B, C and D are reported in Table 2. They are with respect to the catalytic activity measured for catalyst A ($A_{HYD2}$). It can be seen that the performances of catalyst A prepared in accordance with the invention were improved.

The invention claimed is:

1. A catalyst comprising a calcined oxide matrix having alumina content of at least 90% by weight with respect to the total weight of the matrix and an active phase comprising nickel, said active phase being at least partially co-mixed within said calcined oxide matrix a nickel content of 5% to 65% by weight with respect to the total mass of catalyst, said active phase not comprising metal from group VIB, the nickel in the form of particles having a diameter of less than 15 nm, said catalyst having a median mesopore diameter in the range 8 nm to 25 nm, a median macropore diameter of 390 to 800 nm, a mesopore volume, measured by mercury porosimetry, of 0.30 mL/g or more, a total pore volume, measured by mercury porosimetry, of 0.34 mL/g or more, and a macropore volume of 20% to 35% of the total pore volume, and wherein the active phase is entirely co-mixed with the calcined oxide matrix.

2. The catalyst as claimed in claim 1, in which the nickel content is in the range 10% to 34% by weight of said element with respect to the total mass of catalyst.

3. The catalyst as claimed in claim 1, having no micropores.

4. The catalyst as claimed in claim 1, in which the nickel particles have a diameter in the range 1.5 to 12 nm.

5. The catalyst as claimed in claim 1, in which a portion of the active phase is impregnated onto the calcined oxide matrix.

6. A process for the preparation of a catalyst as claimed in claim 1, comprising:
   a) dissolving an acidic aluminium precursor that is aluminium sulphate, aluminium chloride or aluminium nitrate in water, at a temperature of 20° C. to 90° C., at a pH of 0.5 to 5, for a period of 2 to 60 minutes,
   b) adjusting the pH by adding at least one basic precursor that is sodium aluminate, potassium aluminate, ammonia, sodium hydroxide or potassium hydroxide to the suspension obtained in a), at a temperature of 20° C. to 90° C., and a pH of 7 to 10, for a period of 5 to 30 minutes,
   c) co-precipitation of the suspension obtained from b) by adding to the suspension at least one basic precursor that is sodium aluminate, potassium aluminate, ammonia, sodium hydroxide or potassium hydroxide and at least one acidic precursor that is aluminium sulphate, aluminium chloride, aluminium nitrate, sulphuric acid, hydrochloric acid or nitric acid, at least one of the basic or acidic precursors comprising aluminium, the relative flow rate of the acidic and basic precursors being selected in a manner so as to obtain a pH of the reaction medium of 7 to 10 and the flow rate of the acidic and basic precursors containing aluminium being adjusted in a manner so as to obtain a final concentration of alumina in the suspension of 10 to 38 g/L,
   d) filtration of the suspension obtained from the co-precipitation c) in order to obtain an alumina gel,
   e) drying said alumina gel obtained in d) in order to obtain a powder, f) heat treatment of the powder obtained from e) at a temperature of 500° C. to 1000° C., in the optional presence of a stream of air containing up to 60% by volume of water, for a period of 2 to 10 hours, in order to obtain a calcined porous aluminium oxide, g) mixing the calcined porous aluminium oxide obtained from f) with a solution comprising at least one nickel precursor in order to obtain a paste, h) shaping the paste obtained, i) drying the shaped paste at a temperature of 15° C. to less than 250° C., in order to obtain a dried catalyst, j) optionally, a heat treatment of the dried catalyst at a temperature of 250° C. to 1000° C. in the optional presence of water.

7. The process as claimed in claim 6, in which at least one reduction treatment k) is carried out in the presence of a reducing gas after i) or j) in order to obtain a catalyst comprising nickel which is at least partially in the metallic form.

8. The process as claimed in claim 7, in which a passivation l) using a sulphur-containing or oxygen-containing compound or $CO_2$ is carried out before or after the reduction treatment k).

9. The process as claimed in claim 6, in which the concentration of alumina in the suspension of alumina gel obtained in c) is 13 to 35 g/L.

10. The process as claimed in claim 6, in which the acidic precursor of a) and c) is aluminium sulphate, aluminium chloride or aluminium nitrate, and in which the basic precursor of a) and c) is sodium aluminate or potassium aluminate.

11. A hydrogenation process, in which the catalyst as claimed in claim 1 is brought into contact, in the presence of hydrogen, with a feed of hydrocarbons containing polyunsaturated molecules and/or aromatic molecules in a manner such as to obtain an at least partially hydrogenated effluent.

12. The hydrogenation process as claimed in claim 11, in which a selective hydrogenation is carried out at a temperature of 0° C. to 500° C., at a pressure of 0.1 to 20 MPa, at a molar ratio of hydrogen/(polyunsaturated compounds to be hydrogenated) of 0.1 to 10 and at an hourly space velocity of 0.1 to 200 $h^{-1}$ for a liquid feed, of 100 to 15000 $h^{-1}$ for a gaseous feed, of a hydrocarbon feed containing polyunsaturated compounds containing at least 2 carbon atoms per molecule and having a final boiling point of 250° C. or less.

13. The hydrogenation process as claimed in claim 11, in which a hydrogenation of aromatics is carried out at a temperature of 30° C. to 350° C., at a pressure of 0.1 to 20 MPa, at a molar ratio of hydrogen/(aromatic compounds to be hydrogenated) of 0.1 to 10 and at an hourly space velocity of 0.05 to 50 $h^{-1}$ of a feed of hydrocarbons containing aromatic compounds and having a final boiling point of 650° C. or less.

* * * * *